United States Patent [19]

Doerr

[11] Patent Number: 4,578,510

[45] Date of Patent: Mar. 25, 1986

[54] PROCESS FOR MINIMIZING FORMATION OF LOW MOLECULAR WEIGHT OLIGOMERS DURING HYDROLYTIC DEPOLYMERIZATION OF CONDENSATION POLYMERS

[75] Inventor: Marvin L. Doerr, Charlotte, N.C.

[73] Assignee: Celanese Corporation, New York, N.Y.

[21] Appl. No.: 680,441

[22] Filed: Dec. 11, 1984

[51] Int. Cl.$^4$ .......................................... C07C 51/487
[52] U.S. Cl. ................................. 562/483; 562/485; 562/487; 568/858
[58] Field of Search ..................... 562/483, 487, 485; 568/858

[56] References Cited

U.S. PATENT DOCUMENTS 3,120,561  2/1964  Chambret ........................... 562/483

FOREIGN PATENT DOCUMENTS 611032  12/1960  Canada ................................ 562/483

Primary Examiner—Natalie Trousof
Assistant Examiner—Vera C. Clarke
Attorney, Agent, or Firm—Forrest D. Stine

[57] ABSTRACT

A process is described for reducing the amount of low molecular weight oligomers formed during the hydrolysis of a condensation polymer. This process comprises the neutral aqueous hydrolysis of a condensation polymer in which conditions are controlled such that the following two conditions are met:

(1) the amount of water and the condensation polymer present in the hydrolysis zone are such that the least soluble final depolymerization product would not exceed its solubility limits, assuming all of the polymer is converted to final depolymerization products; and (2) temperature conditions and aqueous concentration of final depolymerization products are controlled so that at equilibrium, the amount of low molecular weight oligomers is no greater than 7% of the theoretical, based on the amount of polymer added.

9 Claims, No Drawings

PROCESS FOR MINIMIZING FORMATION OF LOW MOLECULAR WEIGHT OLIGOMERS DURING HYDROLYTIC DEPOLYMERIZATION OF CONDENSATION POLYMERS

BACKGROUND OF THE INVENTION

The invention relates to a process for minimizing the formation of low molecular weight oligomers during the hydrolytic depolymerization of condensation polymers.

The continuous hydrolysis of high molecular weight condensation polymers such as polyethylene terephthalate is well known in the art. Terephthalic acid and ethylene glycol are the primary products of polyethylene terephthalate hydrolysis, a process for the reversal of its polymerization. A by-product produced during such hydrolysis is p-mono(2-hydroxyethyl) terephthalate (MHET) which has the formula:

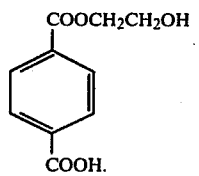

The presence of MHET and other low molecular weight oligomers adversely affects the depolymerization process in three ways:

(1) it interferes with the crystallization of one of the desired products, i.e., terephthalic acid;
(2) it creates difficulties in the liquid-solid separation stage, i.e., isolation of the terephthalic acid from the liquid phase; and
(3) it decreases the yield of the desired end products, i.e., terephthalic acid and ethylene glycol.

As used herein, the term "oligomers" is used to include not only molecules having repeating units, but also half acid adducts, which in the case of polyethylene terephthalate is MHET, and full acid adducts, which in the case of polyethylene terephthalate is p-bis(2-hydroxyethyl) terephthalate (BHET). Such half acid and full acid adducts are the greatly predominating oligomers found in the hydrolysis of condensation polymers.

SUMMARY OF THE INVENTION

Process conditions have now been found for reducing the amount of low molecular weight oligomers formed during the hydrolysis of a condensation polymer. This process comprises the neutral aqueous hydrolysis of a condensation polymer, such as described in U.S. patent application Ser. No. 563,812, filed Dec. 21, 1983, by Jorge W. Mandoki, entitled "Depolymerization of Condensation Polymers", in which conditions are controlled such that the following two conditions are met:

(1) the amount of water and the condensation polymer present in the hydrolysis zone are such that the least soluble final depolymerization product would not exceed its solubility limits, assuming all of the polymer is converted to final depolymerization products; and
(2) temperature conditions and aqueous concentration of final depolymerization products are controlled so that at equilibrium, the amount of low molecular weight oligomers is no greater than 7% of the theoretical, based on the amount of polymer added.

In a preferred embodiment of the invention, temperature conditions and aqueous concentration of final depolymerization products are controlled so that at equilibrium, the amount of low molecular weight oligomers is less than about 5% of the theoretical, based on the amount of polymer added. In the most preferred embodiment, conditions are controlled so that the amount of oligomer is about 3% or less by weight based on the amount of polymer added.

The depolymerization products are recovered from the hydrolysis zone.

DETAILED DESCRIPTION OF THE INVENTION

Condensation polymers which may be hydrolyzed in accordance with the invention are well known in the art and do not per se constitute a part of the invention. Examples of condensation polymers include polyesters obtained by the condensation of a dicarboxylic acid and a dihydric alcohol and characterized by repeating units of the following formula:

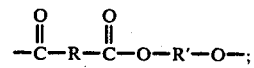

polyamides obtained by the condensation of a dicarboxylic acid and an alkylene diamine characterized by repeating units of the following formula:

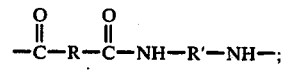

and polycarbonates obtained by the reaction of phosgene and a dihydric phenol and characterized by repeating units of the following formula:

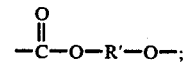

wherein R and R' represent divalent organic radicals. Specific condensation polymers which may be used in the invention include polyethylene terephthalate, polybutylene terephthalate and nylon 66.

Condensation polymer materials which may be used in accordance with the invention may be waste material resulting from the manufacture of articles from the condensation polymers, e.g., waste material which is produced during the production of fibers, chip, film, molded articles such as bottles or the like. The condensation polymer may also be in the form of finished articles, e.g., molded bottles, from which it is desired to reclaim the starting monomers. The condensation polymer is supplied to the aqueous hydrolysis zone in the form of granules or yarns or in some other form suitable for handling.

In a preferred embodiment, the condensation polymer is polyethylene terephthalate and the final depolymerization products are ethylene glycol and terephthalic acid. Of these products, terephthalic acid is the least soluble in water. To minimize the presence of MHET and other low molecular weight oligomers, two criteria should be met. These are:

$$T \leq \frac{2.71828^{(2.90738[P^{0.204192}]-8.09236)}}{100} \quad (1)$$

where T = weight terephthalic acid/weight water; and
P = hydrolysis operating pressure in psi $$0.867M + 140.9T - 8.44MT \leq 7.0 \quad (2)$$

where M = moles water/moles ethylene glycol; and
T = weight terephthalic acid/weight water Equation 1 allows one to calculate the maximum amount of terephthalic acid solubility in water at any given pressure. The second equation permits one to predict the conditions which would allow the depolymerization reaction to go to completion or near completion.

The hydrolysis of polyethylene terephthalate may be conducted in a batch or continuous manner under neutral conditions, i.e., water is the only reactant other than the polyethylene terephthalate, and no bases or acids are added. The hydrolysis reaction is continued until equilibrium conditions have been established. For polyethylene terephthalate, equilibrium is always established in less than 2.0 hours at pressures greater than 400 psi. An ester interchange catalyst as disclosed in Canadian Pat. No. 611,032 may be employed during hydrolysis such as an alkali metal acetate. Following completion of the hydrolysis reaction, it is preferred to cool the reaction mixture over a period of at least 30 minutes since if the cooling of the reaction mixture is instantaneous, the terephthalic acid crystals formed are so minute that they cannot be readily filtered.

In accordance with the invention, there are obtained lower amounts of low molecular weight oligomers such as MHET than by conventional polyethylene terephthalate hydrolysis processes. This is achieved by longer reaction times to allow equilibrium to be reached, higher terephthalic acid concentrations at water/ethylene glycol molar ratios greater than about 20, and higher water/ethylene glycol molar ratios.

Criteria number 2 above may be represented in general terms by the following equation:

$$aM + bT - cMT \leq 7.0$$

wherein M and T are as previously defined. The constants a, b and c were derived for polyethylene terephthalate in the following manner. A similar equation may be derived for different condensation polymers. In a pressurized hydrolysis system, several independent variables are important in determining the quantity of oligomers remaining. These variables include time, temperature or its corresponding pressure, concentration of water, concentration of ethylene glycol, and concentration of terephthalic acid. Since equilibrium conditions must be established, time is no longer an independent variable. It is sufficient to operate at a residence time greater than that required to reach equilibrium. For polyethylene terephthalate, it was found that equilibrium is always established in less than two hours at pressures greater than 400 psi. Thus, time was fixed at two hours and was eliminated as a variable. Temperature or its corresponding pressure is an independent variable which must be included. In a closed aqueous system, pressure is related to the reaction temperature through the formula:

$$\text{Temp.} = 131.854[P^{0.204912}]$$

where temperature is expressed in degrees F and pressure is expressed in psi. (This formula is valid only from 50–1,000 psi.) Since hydrolysis can be run with any water concentration within practical limits, water concentration must remain as an independent variable. If the hydrolysis were always being performed on 100% high molecular weight polyethylene terephthalate, then terephthalic acid and ethylene glycol would always be present in the same ratio and would not be independent variables. However, the hydrolysis of lower molecular weight polyethylene terephthalate oligomers, which contain variable amounts of free ethylene glycol, were also considered as feeds. Thus, the terephthalic acid and ethylene glycol ratio formed upon hydrolysis are not always constant and the two must be treated as independent variables. Thus, this leaves four independent variables which can be reduced to three by defining two convenient ratios as:

M = moles water/moles ethylene glycol
  (after hydrolysis)
T = weight terephthalic acid/weight water
  (after hydrolysis)

This reduces the number of independent variables to three, namely pressure, M and T.

Choosing a high and low level of each of the three variables produces a $2^3$ factorial design requiring eight experiments. In the hydrolysis of other condensation polymers, similar reasoning would also apply.

The experimenter is free to choose any high and low level for each variable within practical limits from which to run the eight experiments and, from each, to determine the level of oligomer (MHET) formed under each condition at equilibrium. For polyethylene terephthalate, the levels chosen were:

Pressure: 400, 900 psi
M: 2, 20 m/m
T: 5, 30 wt/wt

All eight experimental combinations were run at 2 hours residence time followed by overnight cooling. The oligomers (essentially MHET) were isolated by heating the mixture to boiling, filtering hot to remove the insoluble terephthalic acid, while allowing the soluble MHET to pass, followed by crystallization of the MHET from the cooled filtrate. MHET was identified by melting point, thin layer chromatography (TLC) and nuclear magnetic resonance spectroscopy (NMR). Oligomer (MHET) yields were determined gravimetrically. Obviously, for polymers other than polyethylene terephthalate, procedures for isolating the oligomers must be known. Thus, experimental conditions with eight oligomer yields are now available. The method of choice of utilizing these data to predict the oligomer yield, under other conditions, was linear regression analysis. Thus, a general model was chosen to which to fit the data according to the following formula:

% MHET yield = aM + bT + cP + dMT + eMP + fTP + k

| independent variable terms | all interaction terms |
|---|---| where a through f are term coefficients and k = the regression constant

Any method of regression analysis, including computerized software packages, can be used to determine the values of all the coefficients.

In this specific designed experiment, it was found that the pressure (P) term, between 400 and 900 psi, does not not statistically affect the MHET yields, and all terms containing P could be dropped from consideration in the regression model. Thus, the general equation above collapsed to:

$$\% \text{ MHET Yield} = aM + bT + cMT + k$$

The values of the coefficients for polyethylene terephthalate were found to be:
a = 0.867
b = 140.9
c = −8.44
d = −3.4

The "goodness if fit" to a regression model is a statistic known as the regression coefficient ($R^2$). In this case, $R^2 = 0.98$ ($R^2 = 1.00$ is defined as a perfect fit). If, in the case of a designed experiment with other polymers, $R^2$ is below about 0.9, then some important variable was inadvertently eliminated from consideration in the design of the experiments, which then may have to be replanned to increase the value of $R^2$.

Since minimum (or zero) MHET is desired during a hydrolysis operation, the conditions (or region) to operate under are then defined for polyethylene terephthalate as:

$$0.867M + 140.9T - 8.44MT \leq 3.4 \approx 0$$

Ideally, k should be zero, and deviation from zero, in this case, represents experimental error.

The absolute values which are derived from the equations may not be absolutely accurate. However, for any given set of conditions, polymer concentration, temperature, pressure, amount of water, etc., one can take samples and determine whether one is within the parameters of the invention. If oligomer concentration is greater than 7%, one can then use the derived equation to determine how to change conditions to decrease oligomer concentration. For example, if the equation predicted that an oligomer concentration would be 5%, but when one ran the reaction, the actual oligomer concentration was 8%, one would then find different "M" and "T" values to change the yield predicted to, for example, 1.0. This, in turn, would result in a decrease in oligomer concentration below 8%.

A number of experiments were conducted under varying conditions as set forth in Table 1 to establish the criticality of the two criteria set forth above. The results are set forth in Table 1. In this table, experiment 1 utilized conditions wherein neither criteria was met; experiments 2, 3, 4 and 5 utilize conditions where $aM + bT - cMT \leq 7$ was not met; and experiments 6 and 7 utilize conditions where the criteria Act. $T \leq \text{Max. } T$ was not met. Experiments 8–13 utilize conditions wherein both criteria were met. Only in these experiments was the amount of actual MHET obtained less than 7%. In Table 1, "Maximum T" is calculated from equation (1), hereinabove, based on the pressures set forth in Table 1. This equation requires that the "measured T" or "actual T" be less than a calculatable value, determined by solving for the case when "T" is equal to the right side of the equation. Thus, the calculated maximum together with the actual value in each experiment are set forth in the Table.

TABLE 1

| Experiment | Feed Type* | Conditions (psi/hr) | Actual T | Maximum T | Actual M | Value of: aM + bT − cMT | Actual MHET |
|---|---|---|---|---|---|---|---|
| 1 | c | 800/0.5 | 0.344 | 0.284 | 13.1 | 21.8 | 12% |
| 2 | c | 550/3.0 | 0.086 | 0.122 | 52.0 | 19.5 | 18% |
| 3 | c | 800/0.5 | 0.244 | 0.284 | 18.4 | 12.4 | 12% |
| 4 | c | 800/1.0 | 0.246 | 0.284 | 18.3 | 12.5 | 10% |
| 5 | b | 600/3.0 | 0.109 | 0.148 | 78.9 | 11.2 | 18% |
| 6 | b | 300/3.0 | 0.260 | 0.035 | 32.4 | −6.4 | 11% |
| 7 | b | 600/4.0 | 0.260 | 0.148 | 32.4 | −6.4 | 11% |
| 8 | a | 800/0.5 | 0.209 | 0.284 | 43.9 | −9.9 | 1% |
| 9 | a | 800/0.5 | 0.209 | 0.284 | 43.9 | −9.9 | 4% |
| 10 | a | 800/0.5 | 0.209 | 0.284 | 43.9 | −9.9 | 3% |
| 11 | a | 800/0.5 | 0.209 | 0.284 | 43.9 | −9.9 | 2% |
| 12 | a | 800/0.5 | 0.209 | 0.284 | 43.9 | −9.9 | 1% |
| 13 | a | 800/0.5 | 0.209 | 0.284 | 43.9 | −9.9 | 0.1% |

*a = 100% high molecular weight PET feed
b = 90% high molecular weight PET/10% low molecular weight feed
c = low molecular weight PET feed Although the invention has been described in considerable detail with particular reference to certain preferred embodiments thereof, variations and modifications can be affected within the spirit and scope of the invention as described hereinbefore, and as defined in the appended claims.

What is claimed is:

1. A process for the depolymerization of a condensation polymer selected from the group consisting of polyesters, polyamides and polycarbonates which comprises subjecting said polymer to neutral aqueous hydrolysis while controlling the conditions such that the following two conditions are met:
   (1) the amount of water and the polymer addition level are such that the least soluble depolymerization product does not exceed its solubility limits, assuming all of the polymer is converted to depolymerization products; and
   (2) temperature conditions and aqueous concentrations of final depolymerization products are controlled so that at equilibrium the amount of low molecular weight oligomers is no greater than 7% of the theoretical, base on the amount of polymer used, and recovering the depolymerization products from the hydrolysis zone.

2. A process as defined in claim 1 wherein said condensation polymer is a polyester.

3. A process as defined in claim 2 wherein said polyester is polyethylene terephthalate.

4. A process as defined in claim 3 wherein conditions are adjusted so as to meet the following two criteria:

$$T \leq \frac{2.71828^{(2.90738[P^{0.204192}] - 8.09236)}}{100} \quad (1)$$

where T = weight terephthalic acid/weight water; and
P = hydrolysis operating pressure in psi; and $$0.867M + 140.9T - 8.44MT \leq 7.0 \quad (2)$$

where M = moles water/moles ethylene glycol and T = weight terephthalic acid/weight water.

5. A process as defined in claim 4 wherein said reaction mixture is cooled over a period of about 30 minutes and terephthalic acid crystals formed during hydrolysis are recovered by filtration.

6. A process as defined in claim 1 wherein the temperature conditions and aqueous concentrations of final depolymerization products are controlled so that at equilibrium the amount of low molecular weight oligomers is less than about 5% of the theoretical, based on the amount of polymer used.

7. A process as defined in claim 1 wherein the temperature conditions and aqueous concentrations of final depolymerization products are controlled so that at equilibrium the amount of low molecular weight oligomers is less than about 3% of the theoretical, based on the amount of polymer used.

8. A process as defined in claim 3 wherein the temperature conditions and aqueous concentrations of final depolymerization products are controlled so that at equilibrium the amount of low molecular weight oligomers is less than about 5% of the theoretical, based on the amount of polymer used.

9. A process as defined in claim 3 wherein the temperature conditions and aqueous concentrations of final depolymerization products are controlled so that at equilibrium the amount of low molecular weight oligomers is less than about 3% of the theoretical, based on the amount of polymer used.

* * * * *

UNITED STATES PATENT AND TRADEMARK OFFICE
CERTIFICATE OF CORRECTION

PATENT NO. : 4,578,510

DATED : Mar. 25, 1986

INVENTOR(S) : Marvin L. Doerr

It is certified that error appears in the above-identified patent and that said Letters Patent is hereby corrected as shown below:

Column 5, line 18, "d=-3.4" should be corrected to read -- k=-3.4 --.

Signed and Sealed this

Fourth Day of November, 1986

[SEAL]

Attest:

DONALD J. QUIGG

Attesting Officer

Commissioner of Patents and Trademarks